(12) United States Patent
McGlynn et al.

(10) Patent No.: US 8,202,202 B2
(45) Date of Patent: Jun. 19, 2012

(54) WEB ENABLED INTERACTIVE AEROBIC TRAINING SYSTEM

(76) Inventors: Thomas Lee McGlynn, Burlingame, CA (US); Renganathan Sreenivasan, San Ramon, CA (US)

( * ) Notice: Subject to any disclaimer, the term of this patent is extended or adjusted under 35 U.S.C. 154(b) by 0 days.

(21) Appl. No.: 12/321,087

(22) Filed: Jan. 15, 2009

(65) Prior Publication Data

US 2010/0179027 A1    Jul. 15, 2010

(51) Int. Cl.
*A63B 71/00* (2006.01)
(52) U.S. Cl. ............................................................ 482/9
(58) Field of Classification Search ................... 482/1, 8, 482/9
See application file for complete search history.

(56) References Cited

U.S. PATENT DOCUMENTS 6,039,688 A * 3/2000 Douglas et al. ............... 600/300
7,558,526 B2 * 7/2009 Guo .............................. 455/3.06
2006/0230102 A1 * 10/2006 Hidary ........................... 709/203
2008/0051993 A1 * 2/2008 Graham et al. ................ 701/209
2008/0300498 A1 * 12/2008 Edwards ........................ 600/520
2010/0035725 A1 * 2/2010 Rickerman ........................ 482/8
2010/0057848 A1 * 3/2010 Mangold ........................ 709/203

* cited by examiner

*Primary Examiner* — Steve R Crow
*Assistant Examiner* — Shila Jalalzadeh Abyane
(74) *Attorney, Agent, or Firm* — Jonathan Pena

(57) ABSTRACT

An athletic training system is described herein. The training system is accessed by a computer system enabled for accessing the internet through a known web browser. The computer system accesses the athletic training system that accepts user input including at least past performance in a race or time trial, generates a pace chart based on that performance which pace chart defines the user's current fitness status and appropriate training intensity, and generates a training program that considers at least the fitness level of the user as indicated by the pace chart and the races the user plans to run. The training program is populated from a database containing many different classes of workouts, a different mix of the stored workouts providing optimum training for races of different distances. In an embodiment of the present invention, the system may provide access to a coach who can answer user questions or change the automatically generated workout schedule to accommodate particular concerns.

18 Claims, 8 Drawing Sheets

Continued from Fig 3a.

---

Get the Following Class of Attributes:
1. Athlete's Preferences such as Track Access/Treadmill Access/ Access to a Measured Course/ GPS No. of running days per week, No. of Cross Training Days. Athlete's preferred Schedule.

2. Athlete's Fitness Level – This is derived based on last race result. For Example: Brand New ( 5K time slower than 32 minutes), Intermediate ( 5K time between 26 and 32 minutes), Advanced (5K time between 22 and 26 minutes), Boston Qualifier( 5K time between 19 and 22), Regional Elite (5K time between 16 and 19), Elite ( 5K time faster than 16 minutes)

3. Athlete's Running and Training Experience. For example: Longest Historical Week, Number of Years of Running, Longest Run done in the last 8 weeks, Longest Run in the last 1 year, Longest Historical Run, Average No. of Miles Per Week over the last 4 weeks, last 1 Year, last 10 Years.
4. Athlete's Health Information like Sickness, Injuries – For example: Viral Fever, Stress Fracture, Ligament Injury, Weak Knee, Hip, etc.. (125)

---

Based on the Goal Race, and the above attributes, Determine the Workout Types or Categories that Athlete needs to do for the Remaining time Period. For Example: A typical Marathon training might include 1 Long Run, 1 Maintenance Run, 1 Track Workout, 1 Threshold/Tempo Run per week. Mileage and Distance varies for each week. (127)

---

Calculate the Total Mileage for Each Week upto the Race Day. Appropriately, allocate the mileage for Long Runs for each week, Maintenance Runs , Track Workouts and Threshold workouts. (129)

---

1. Select the Applicable Workouts based on all the above attributes( Attributes are the Qualifiers) and based on Intensity, Rank defined in Workout Templates. For a detailed explanation of how Workout Qualifiers work, Please refer to Workout Qualifiers Diagram.
2. Create/Update the Workout Calendar for the current season. (131)

---

End (133)

Fig. 4

Pace Chart

300

Pace Chart for Renga Sreenivasan based on a selected vVO2 of 260    Printable version for Pace Chart

| vVO2:260 | 800m | 1500m (1 Mi) | VO2 (2 Mi) | 5K (3 Mi) | 10K (6 Mi) | Threshold | 1/2 Marathon | 80% | Maintenance | Marathon |
|---|---|---|---|---|---|---|---|---|---|---|
| 200m (1/2 lap) | 0:39 | 0:43 | 0:46 | 0:48 | 0:49 | 0:52 | 0:53 | 0:57 | 1:01 | 0:55 |
| 400m (1 lap) | 1:19 | 1:26 | 1:32 | 1:36 | 1:39 | 1:45 | 1:46 | 1:54 | 2:03 | 1:50 |
| 600m (1.5 laps) | 1:59 | 2:10 | 2:19 | 2:24 | 2:29 | 2:38 | 2:39 | 2:52 | 3:04 | 2:45 |
| 800m (2 laps) | 2:38 | 2:53 | 3:05 | 3:12 | 3:19 | 3:31 | 3:32 | 3:49 | 4:06 | 3:41 |
| 1200m (3 laps) | 3:58 | 4:20 | 4:38 | 4:48 | 4:59 | 5:16 | 5:18 | 5:44 | 6:09 | 5:31 |
| 1600m (1 Mi) | 5:17 | 5:47 | 6:11 | 6:24 | 6:39 | 7:02 | 7:04 | 7:39 | 8:12 | 7:22 |

Your estimated Half-Marathon time is:  1:33:20
Your estimated Marathon time is:  3:14:27

Fig. 5

(a) 3
Track:
Michigan =
1200m@10K rit
1600m@80% rit
800m@10K rit
1600m@80% rit
400m@VO2
pace
(don't run the
400m any faster
than VO2)
Mileage: 6-7

(b) 24
Track:
Bondarenko
Continuous = 2X,
1X {400m@5K,
400m@80%,
300m@VO2,
300m@80%,
200m@1500m
pace,
200m@80%,
100m hard,
100m@80%}
400m easy jog
recovery after first
2
Mileage: 5-6

(c) 29
Track: SPECIAL
LOCATION=
STANFORD DISH =
Junipero Serra/
Campus Dr
Intersection (North
Entrance)
2x600m hill @ 5K
effort (600m jog
recovery);
4-8x200m @ 1500m
effort (200m jog
recovery)
Mileage: 5-7

(d) 21
Track: Lane 8
Tempo run (12-16
laps @ 10K pace)
Mileage: 6-8

Workout Schedule for Tom Hancock

Printable version of Workout Schedule

January 2009

| Sunday | Monday | Tuesday | Wednesday | Thursday | Friday | Saturday |
|---|---|---|---|---|---|---|
| 28 Recovery: Active recovery Mileage: 0-0 | 29 Track: MIT Track or 6x800m @ 5K (2:00 jog) + Workout with Trainer Mileage: 5-6 | 30 Cross Training: 45-60 mins. with HR @ 65-80% of MHR Aerobic cross training Mileage: 0-0 | 31 Maintenance: 50-55 mins. @ maintenance pace. Mileage: 6-6 | 1 Maintenance: Happy New Year! 2009 will be super Fine! Get out for a good 60:00 @ maintenance pace. Mileage: 6-7 | 2 Cross Training: 45-60 mins. with HR @ 65-80% of MHR Aerobic cross training Mileage: 0-0 | 3 Long Run: 120 mins. @ maintenance pace. Mileage: 13-13 |
| 4 Maintenance: Easy 30-45 mins. Mileage: 4-5 | 5 Track: MIT Track: Good warmup/cool down and drills (no more than 5k @ VO2/5K with good recovery) + workout with trainer Mileage: 6-7 | 6 Cross Training: 45-60 mins. with HR @ 65-80% of MHR Aerobic cross training Mileage: 0-0 | 7 Maintenance: 50-55 mins. @ maintenance pace. PM: fly to LA Mileage: 6-6 | 8 Track: WUP; Fartlek = 3:00 on (~10K) right into 1:00 of (~80%); 4:00 on/1:30 off; 5:00 on/2:00 off; 6:00 on/2:30 off; 5:00 on/2:00 off; 4:00 on/1:30 off; 3:00 on/1:00 off; CDP Mileage: 7-8 | 9 Recovery: AM: 35-40 mins. @ maintenance pace. PM: fly to Australia Mileage: 4-4 | 10 Day Off: Travel to Australia Mileage: 0-0 |
| | | | | | | Mileage: 30-32 |
| | | | | | | Mileage: 27-30 |

WEB ENABLED INTERACTIVE AEROBIC TRAINING SYSTEM

BACKGROUND

1. Field of the Invention

The present invention relates to computerized systems for athletic training. More specifically, it relates to a web-enabled computerized training system wherein training programs are generated for different aerobic athletes based on each athlete's particular current athletic capabilities and future goals.

2. Related Art

As participation in various aerobic sports has increased in recent years, the need for coaching in these sports has also increased. One-on-one coaching for each particular sport remains, perhaps, the gold standard, but such instruction and assistance is always expensive and may not be available in every area for every participant.

With respect to running in particular, individual coaching is generally limited to participants in High School or college athletic programs. As running has become an increasingly popular aerobic sport (15 million people living in the U.S. run 100 or more days a year), more and more amateur adults are entering races and seeking out coaching in one form or another to enable them to improve their performance and avoid injury.

In an attempt to provide training assistance and protocols to a larger group of participants, various training programs have been offered that use a computer to deliver a workout plan. Generalized training programs are also offered over the interne. To date, these known computerized training programs have met with limited acceptance and success. The known programs typically present a generic training plan that admits of very little in the way of individual optimization. For example, a twelve-week training program for a 10 Kilometer (K) race is presented, offering daily mileage to be run. Some versions offer different levels of the program to accommodate beginning, intermediate and advanced runners, each level offering progressively more difficult workouts. Further, some programs offer some additional customization by detailing the type of workout on each day. A few examples of different workouts would be hill training and interval training (of various kinds).

What known training programs collectively lack is any true customization based on an individual's current fitness level, athletic background and desired goals. An exercise training program that could offer such individualized training programs through a standard and known interne web browser would be highly desirable.

SUMMARY

One embodiment of the present invention relates to a computer system enabled for accessing the interne through a known web browser. The computer system accesses an athletic training site that contains a database of runner level's, workouts, and individual data such as age, sex etc. From this database it assigns a current fitness level to the athlete, based on a call to the pace chart generator that accepts either actual previous race performance or information recorded by the individual through a personal time trial. The system uses these data to generate a pace chart, a calendar populated by races the individual intends to run, and calls a training program generator that considers at least the fitness level of the individual as indicated by the pace chart generator and the races the individual plans to participate in and generates a workout schedule using that information, thus generating a customized training program.

Further customization is readily permitted by this system. Injuries, a common enough difficulty for many runners, can be entered into the appropriate page of the individual's profile database and then considered when generating the final training schedule or editing an existing training schedule. As many runners, especially those new to the sport, set unrealistic goals in light of their current fitness level, their current injury status or both, the system is designed to inform the individual when goals and current abilities cannot be aligned in the projected time span. If a new runner states that he wants to run a marathon in a month and has a sprained ankle, the system will warn him that such a goal at this time is unrealistic and dangerous and will propose rather a period of recuperation and then incremental training over a period of time that is appropriate to the distance of the desired race.

An additional feature will allow different individuals to compare their respective training programs and to coordinate their efforts, as they mutually desire. A runner from Boston, Mass. who is visiting Palo Alto, Calif. could query the system to see if any other users live in that area and if they would be interested in running with the visitor. The visitor could also query local runners for desirable running routes and locations through the system.

Although the invention will be discussed primarily in terms of running, nothing herein restricts its applicability to that sport alone. The same pace chart generator could be modified as needed to accommodate any aerobic sport, including swimming, cycling, speed-skating, cross-country skiing, etc. Indeed, based on an athlete's individual preference, workouts involving other sports, frequently called cross-training, can be readily incorporated into that athlete's training schedule, even further optimizing the training for a particular individual.

BRIEF DESCRIPTION OF THE FIGURES

FIGS. 3a and 3b are a flow chart showing how the athletic coaching system operates in accordance with an embodiment of the present invention;

Note that like reference numerals refer to corresponding parts throughout the drawings.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Figure 1:
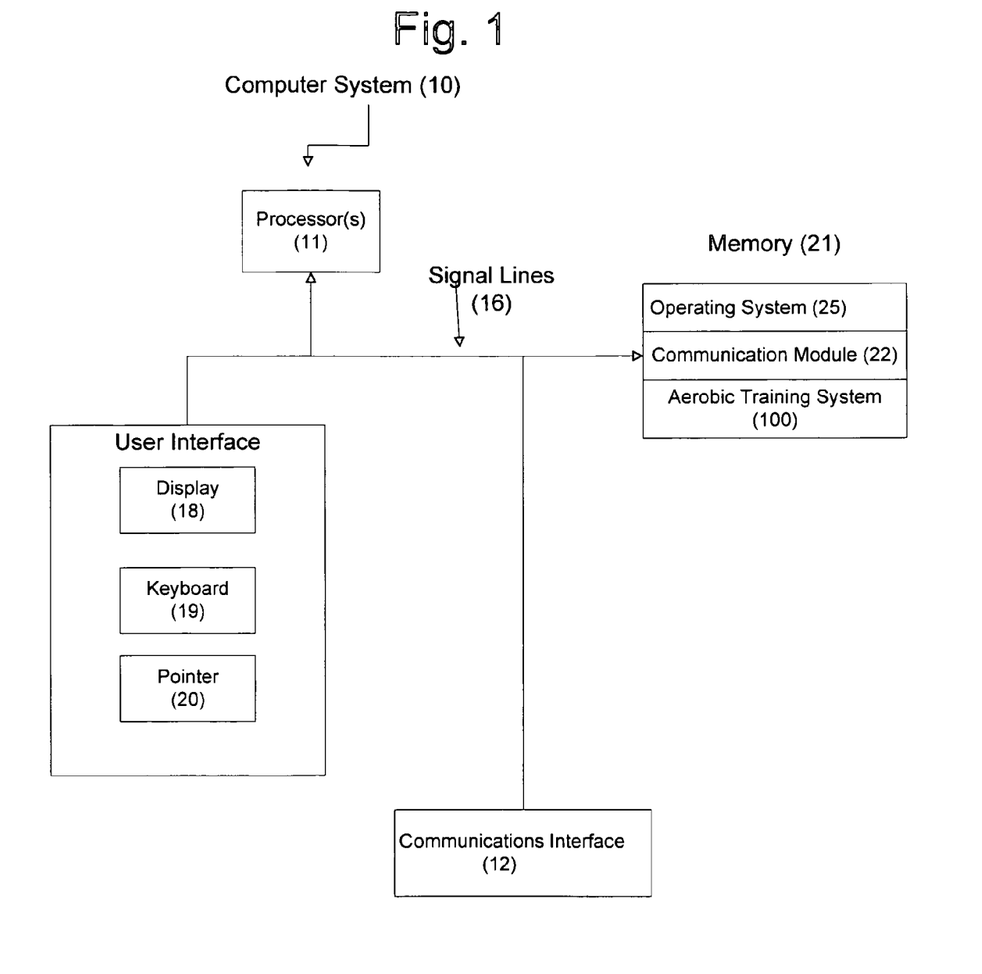
FIG. 1 is a diagram of a web-enabled general purpose computer system capable of operating the athletic coaching system in accordance with an embodiment of the present invention.

FIG. 1 presents a block diagram illustrating a computer system 10 that performs the athletic coaching system of the present invention. Computer system 10 includes one or more processors 11, a communication interface 12, a user interface 14, and one or more signal lines 16 coupling these components together. Note that the one or more processing units 11 may support parallel processing and/or multi-threaded operation, the communication interface 12 may have a persistent communication connection, and the one or more signal lines 16 may constitute a communication bus. Moreover, the user interface 14 may include: a display 18, a keyboard 19, and/or a pointer 20, such as a mouse.

Memory 21 in the computer system 10 may include volatile memory and/or non-volatile memory. More specifically, memory 21 may include: ROM, RAM, EPROM, EEPROM, flash memory, one or more smart cards, one or more magnetic disc storage devices, and/or one or more optical storage devices. Memory 21 may store an operating system 25 that includes procedures (or a set of instructions) for handling various basic system services for performing hardware-dependent tasks. Memory 21 may also store procedures (or a set of instructions) in a communication module 22. These communication procedures may be used for communicating with one or more computers and/or servers, including computers and/or servers that are remotely located with respect to the computer system 10.

Figure 2:
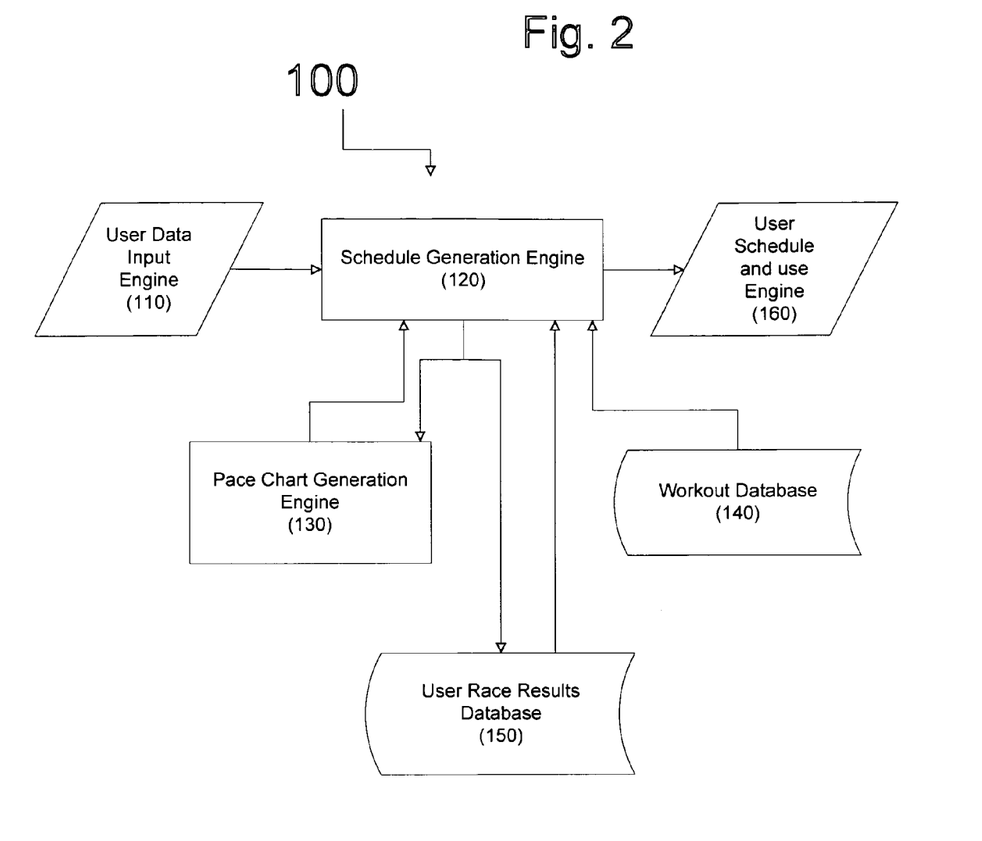
FIG. 2 is a block diagram of the athletic coaching system in accordance with an embodiment of the present invention.

Memory 21 may also include a program module 100 (or a set of instructions) that comprise a first embodiment of the present invention. FIG. 2 provides a detailed block diagram of the program module that comprises this first embodiment of the present invention and will be described in detail below. Instructions in the various modules in the memory 21 may be implemented in: a high-level procedural language, an object-oriented programming language, and/or in an assembly or machine language. In a first embodiment of the present invention, the databases are implemented using MySQL and the program itself uses PHP, a common open source programming language. Note that the programming language may be compiled or interpreted, e.g., configurable or configured, to be executed by the one or more processing units 11.

Although the computer system 10 is illustrated as having a number of discrete items, FIG. 1 is intended to be a functional description of the various features that may be present in the computer system 10 rather than a structural schematic of the embodiments described herein. In practice, and as recognized by those of ordinary skill in the art, the functions of the computer system 10 may be distributed over a large number of servers or computers, with various groups of the servers or computers performing particular subsets of the functions. In some embodiments, some or all of the functionality of the computer system 10 may be implemented in one or more application-specific integrated circuits (ASICs) and/or one or more digital signal processors (DSPs).

Computer system 10 may include one of a variety of devices capable of manipulating computer-readable data or communicating such data between two or more computing systems over a network, including: a personal computer, a laptop computer, a mainframe computer, a portable electronic device (such as a cellular phone or PDA), a server and/or a client computer (in a client-server architecture). Moreover, the network may include: the Internet, World Wide Web (WWW), an intranet, LAN, WAN, MAN, or a combination of networks, or other technology enabling communication between computing systems. A first embodiment of the present invention envisions program module 100 running on a computer system 10 configured as a server and multiple users accessing the server through remote computer systems using common communications channels such as the Internet and WWW, using known computer communications programs and protocols.

Computer system 10 may include fewer components or additional components. Moreover, two or more components may be combined into a single component, and/or a position of one or more components may be changed. In some embodiments, the functionality of the computer system 10 may be implemented more in hardware and less in software, or less in hardware and more in software, as is known in the art.

FIG. 2 is a detailed block diagram of program module 100 shown in FIG. 1 and comprises a first embodiment of the present invention. In this description, program module 100 shall be referred to as the aerobic training system or system.

System 100 is comprised of at least a user data input engine 110, a schedule generation engine 120 coupled to data input engine 110, a pace chart generation engine 130 coupled to the schedule generation engine 120, a user's race result database 150 coupled to the schedule generation engine 120, a workout database 140 coupled to the schedule generation engine 120 and a user schedule and use engine 160 coupled to the schedule generation engine 120.

User data input engine 110 provides a user input interface for the athletes (referred to as runners henceforth but the present invention is in no way limited to use only by runners) to provide data to system 100. Such data would include the runner's age, sex, running history, including weekly mileage, longest run in the last four weeks and the longest run ever, track access, Global Positioning System (GPS) device ownership, measured distance route availability, treadmill access, race or time trial results, running goal(s) and injury status, which would further include nature of the injury as appropriate. This data is provided to schedule generation engine 120.

Schedule generation engine 120 receives the runner's data from user data input engine 110 and provides at least the sex, age and race/time trial results to pace chart generation 130.

Figure 3A:
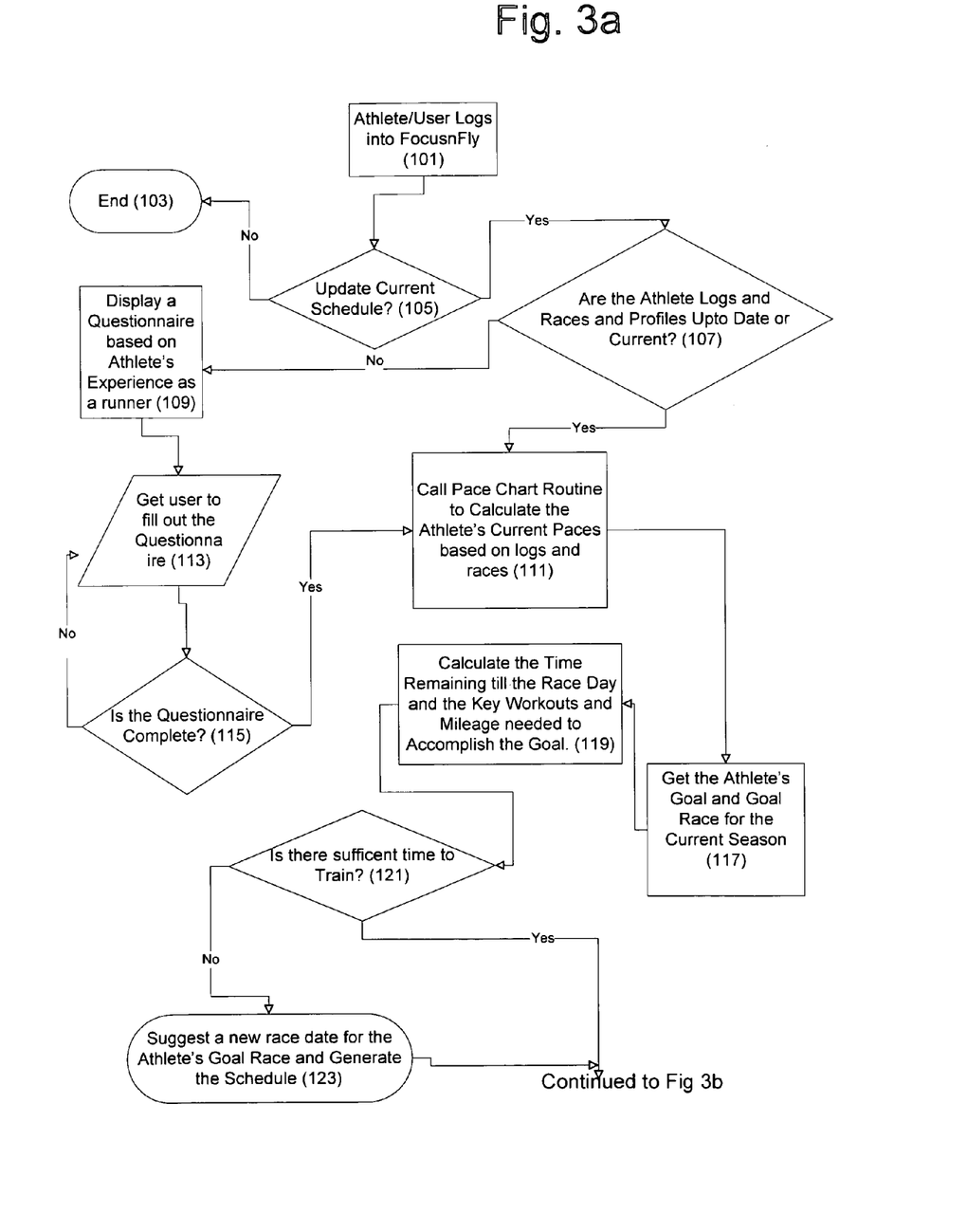

Pace chart generation engine 130 uses the data received from schedule generation engine 120 to generate a runner pace chart, which pace chart will be more fully described with reference to FIGS. 3a, 3b and 4 subsequently. The pace chart is then communicated to schedule generation engine 120.

Using the runner data received from the user data input engine 110, the pace chart received from pace chart generation engine 130, and runner race result data, which is received from user data input engine 110 and which is passed through schedule generation engine 120 for storage in the user race results database 150, the schedule generation engine 120 selects appropriate workouts from the workout database 140 to generate a runner's training schedule. The methods used by schedule generation engine 120 to select appropriate workouts from the workout database in conjunction with the information received from the runner through the user data input engine 110, the pace chart generated by pace chart generation engine 130 and user race results from the user race results database 150 will be more fully described with reference to FIGS. 3a and 3b subsequently.

User Schedule and Use engine 160 is coupled to the schedule generation engine and presents the completed schedule to the runner. Engine 160 is also enabled to allow some types of communication through computer system 10 (FIG. 1) with other runners who are authorized to use system 100. If an athletic coach is involved who supervises the operation and use of system 100, then such supervision would occur through user schedule and use engine 160. However, as system 100 provides an individualized training schedule without the intervention of a coach or other person, such coaching is not an essential element of the present invention. Such communication permits mutual exchange of training schedules and coordination between runners to train together as mutually desired and allows the coach to respond to questions and concerns of the runner regarding his or her schedule.

The process by which an individual runner interacts with system 100 (FIG. 2) and by which system 100 generates a customized athletic training program is described with reference primarily to FIGS. 3a and 3b. The description of the operation of the system will reference the user as a runner. As previously mentioned, although a first embodiment of the present invention is focused on runners as the primary users, nothing herein should be taken to limit the present invention to the generation of training programs for runners only. With appropriate modification to pace chart generation engine 120 and workout database 140 (FIG. 2), the present invention can generate training schedules for cyclists, swimmers, triathletes or any other group of athletes.

With reference again to FIGS. 3a and 3b, each runner who is allowed to use system 100 chooses a user name and selects a password. Entry of the user name and password gives access to system 100 at step 101.

If the runner is logging in simply to check his or her existing training schedule (step 105), such review requires system 100 to take no further action other than permitting the runner to review the training schedule (step 103). However, if the runner wishes to update or modify the current training schedule, or if the runner is using system 100 for the first time, further action is required and that action begins at step 107.

At step 107, the system queries the runner as to whether the runner's running logs (record of the miles run in the past four weeks, longest run in the last four weeks, etc.), races (record of recorded times in previous races as well as their distance and also future planned races) and runner profile are current. A runner could also indicate that this is a first time use of system 100.

System directs all new runners and all runners who wish to update their training schedule to step 109 from step 107. A questionnaire is presented by means of the user data input engine 110 (FIG. 2) to determine the runner's current ability and future goals. The questionnaire will minimally require that the runner enter or update his or her current mileage (weekly mileage, mileage in the last four weeks, longest run in four weeks, etc.) and training experience, time in a recently run race, as well as that race's distance (alternatively, a time for a measured distance, not an official running event, can be entered), whether the runner has access to a track or not, owns a GPS device, treadmill access, current health status, with further follow-up questions appearing depending on that health status. For example, if a runner indicates that he or she is not well, the system will present questions to determine the nature of the injury. A cold will, for example, only present a minor impediment to training, whereas a severely sprained ankle will present a much more significant one. The runner fills out the questionnaire at step 113. Until the questionnaire is complete, as determined by system 100 at step 115, the system loops back to step 113.

Once the questionnaire is complete, the pace chart generation engine 130 is called at step 111. The pace generation engine 130 uses the distance run/time entered by the runner into the questionnaire at step 113 to generate a pace chart. A sample pace chart is shown in FIG. 4. Pace chart generation engine 130 normalizes the data provided by the runner and generates a velocity at maximal oxygen consumption speed, represented here by the formula $v@VO_2$, where v represents velocity in meters per second, V represent Volume in milliliters per kilogram of body weight and $O_2$ is gaseous oxygen. From this one pace, the pace chart generation engine 130 calculates the other paces required to populate a pace chart. In the pace chart of FIG. 4, the pace equivalent of running at $v@VO_2$ is represented by the shorthand of VO2. In this manner, a runner's current ability as demonstrated in actual races or time trials is used to generate a range of training speeds by the pace chart generation engine 130.

Figure 4:
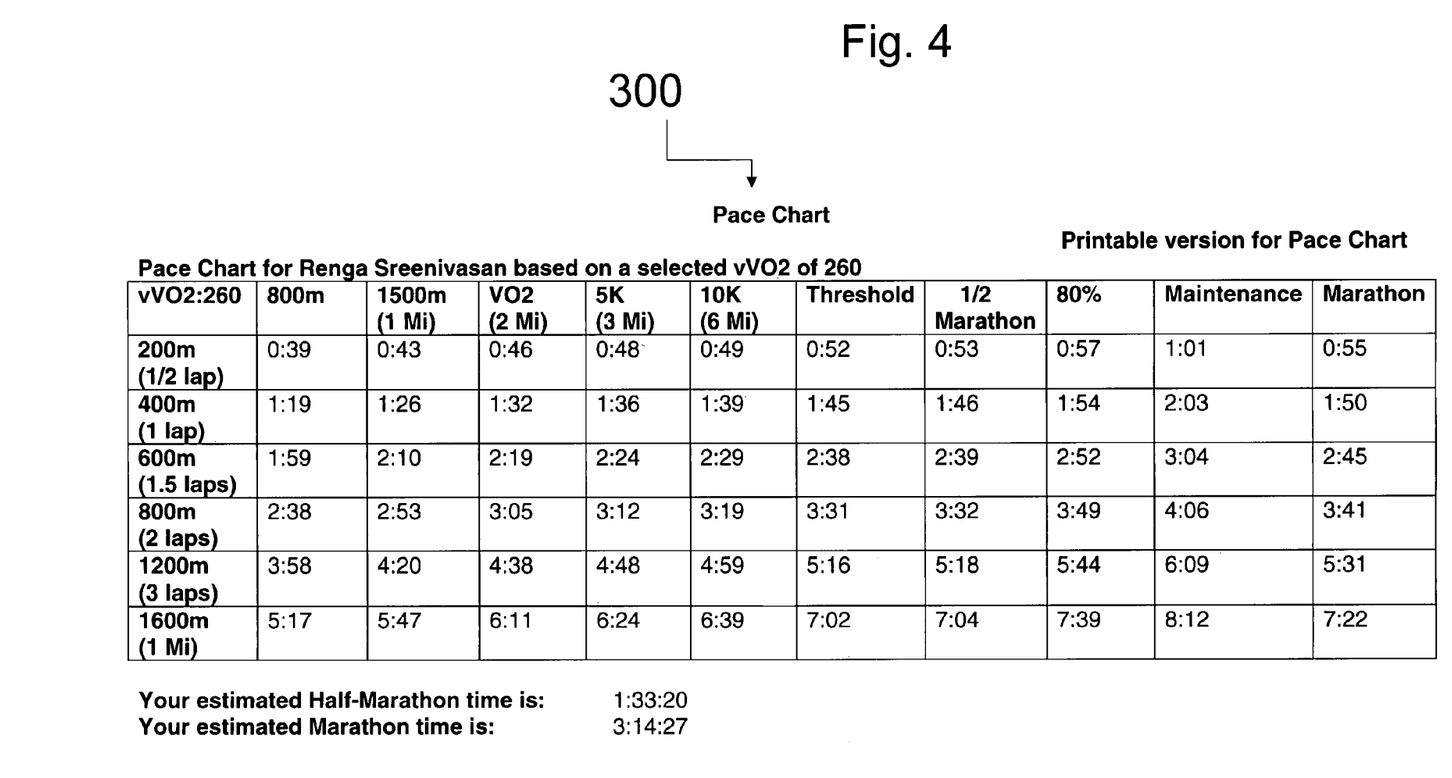
FIG. 4 is a sample pace chart according to an embodiment of the present invention.

As shown in FIG. 4, pace chart 300 is labeled across its x-axis with different paces—in this example, 800 m pace, 1500 m pace, VO2 pace, 5K pace, 10K pace, threshold pace, ½ Marathon pace, 80% pace, maintenance pace and Marathon pace. These are derived from the $v@VO_2$ pace determined by an actual race or time trial run and entered by the runner. From right to left, they represent increasingly fast running paces. The chart's y-axis is labeled with different distances, ranging from 200 meters (hence "m") to 1,600 m. Extension of the chart to include other distances along the y-axis would be an obvious modification to this embodiment.

In use, a workout schedule might call for the runner to run four 1200 m intervals at 10K pace. In chart 300, this would mean that the runner should run each interval in 4 minutes, 59.4 seconds. In training, especially with beginning runners, there is a tendency, especially when doing interval training, for the runner to try and run each interval as quickly as possible. This is almost always counter-productive. The runner usually gets injured relatively soon in this scenario and interval workouts become a dreaded part of the training program, if they remain part of it at all. By providing very clear guidance on how fast to run each interval and by insuring that the paces are within a runner's capacity, the pace generation system forms an important element of the present invention. Additionally several individual physiological contributors to success at endurance competitions are all improved by performing the scheduled workouts at the specified pace. These physiological contributors are: a) aerobic economy, which measures how efficiently oxygen is utilized by the runner to maintain a given pace; b) anaerobic threshold, which is the maximum level at which the runner can operate before cellular metabolism requires anaerobic energy generation; c) $VO_2$ maximum, which is the most intense level or speed that the runner can run wherein cellular metabolism is primarily aerobic; d) neurological-muscular stamina, the ability of the brain and muscles to operate together efficiently over an increasing period of time; and e) glycogen storage development, which is the ability of cells to store and use more glycogen after proper training.

Referencing again to FIGS. 3a and 3b, after generation of pace chart 300 at step 111, the system proceeds to step 117 where the schedule generation engine 120 (FIG. 2) retrieves the runner's next running goal (e.g., run a Half Marathon in less than 1 hour and thirty minutes) and the race the runner wants to run in order to achieve the goal (e.g., the Monterey Half Marathon).

The system then calculates the time remaining to the race (with appropriate error messages if the race day has already passed!) at step 119. If system 100 determines at step 121 that there is insufficient time remaining to adequately train for the race given the runner's current fitness level, system 100 will generate a message for display that the goal and timing are unrealistic and suggests that the runner select another race that can be used as input for the schedule generation engine 120.

If there is sufficient time to train (either for the originally selected race or the alternative race requested by the system,) system 100 next uses the data the runner provided at step 113 and the v@VO$_2$ pace from the pace chart generation engine 130 to assign the runner a fitness level. In a first embodiment of system 100, a runner may be one of six fitness levels: beginner, intermediate, advanced, Boston Marathon Qualified, Regional Elite and Elite. Each level represents increasing aerobic fitness and a faster v@VO$_2$ pace. This assessment occurs at step 125. The other runner data provided at step 113, such as access to a track, treadmill access, number of days run per week and number of cross-training days per week, along with running and training experience (longest historical weekly mileage, number of years running, longest run in the previous four weeks, experience with track workouts) and athlete health and injury information is also arranged and codified by the schedule generation engine 120 at step 125 in preparation for the actual generation of a training schedule.

It should be stressed that the system will provide warnings to the runner and the system administrator (the coach), if one is involved, if the runner's health and injury status indicates that the runner cannot safely prepare for or run the planned race.

Based on the information gathered at step 125, schedule generation engine 120 determines the workout types that the runner must do in the time remaining before the race to adequately train for that race at step 127. Although not specifically enumerated in step 127, schedule generation engine 120 also takes into consideration a training concept called periodization. Periodization is the idea that maximum training load (weekly mileage) and maximum intensity (interval workouts of increasing stress) need to be scheduled so that the runner has time to assimilate their benefit as well as time to recover from them and to be properly rested before the race (conditioning effect). For example, a runner choosing to do a Marathon will see a schedule with his or her highest weekly mileage sometime in the month before the event. As the race approaches, the runner's schedule will call for less weekly mileage but some of that mileage may still be intense (interval workouts) so that the runner can be kept at the peak of conditioning but not overly tired.

As shown in step 127, and purely as one possible example, the runner has been assigned one long run, two shorter maintenance runs and 1 track workout/threshold/tempo run per week.

Having determined the types of workouts required for the runner at step 127 (FIGS. 3a and 3b), the schedule generation engine 120 (FIG. 2) next calculates at step 129 the total mileage the runner should run each week based on his or her fitness level and the other runner information earlier received. Schedule generation engine 120 assigns an appropriate number of miles to each of the different classes of workouts.

Although these calculations occur automatically, the system always permits the system operator, typically the athletic coach, to intervene. A relatively new runner who has already run a sub-forty minute 10K race may be able to adequately prepare for a sub-one hour and thirty minute Half Marathon in a relatively short period of time, with relatively higher mileage, whereas a novice, even with a year to train, might find that goal too difficult. The coach can always adjust the training schedule or communicate directly with the runner to adjust weekly mileage to compensate for injury, varying performance and life issues that may take precedence over running.

An important element of the present invention is the database of different workouts classified according to at least the type of workout, its stress level, purpose, and track availability. Different kinds of running workouts prepare the runner for different races. These workouts stress and develop the aforementioned physiological contributors in periodized approach. For example, a person training for a short race such as an 800 m sprint needs to do many more short, very high speed, high stress intervals than someone preparing for a Marathon. The latter would generally require workouts that increase long duration stamina at a somewhat slower speed. It is not, however, correct that the long-distance runner will never need to perform short, high-intensity intervals or that the sprinter will never do a long, relatively slowly paced workout. Depending on where each individual runner is in their training cycle, different workouts may be appropriate. Even relatively short races such as an 800 m sprint require a large aerobic capacity and even in the Marathon a runner needs a certain minimum of anaerobic capacity.

Four representative workouts from the workout database 140 (see FIG. 2) are shown in FIGS. 5a, 5b, 5c and 5d. FIG. 5a is called a "Michigan." The runner runs a 1200 m interval at his or her 10K pace, immediately followed by a 1600 m interval at that runner's 80% pace, followed immediately by an 800 m interval at 5K pace, another 1600 m interval at 80% pace and a final 400 m interval at VO$_2$ pace. The starting distance of the Michigan can be increased, which would consequently increase the total number of intervals in the workout and the total distance. Such increases would occur as a runner peaks for a long race, acclimates to the training and can perform at the higher level without unduly risking injury FIG. 5b shows what is known as a "Bondarenko." A 400 m interval at 5K pace is followed by a 400 m interval at 80% pace, a 300 m interval at VO$_2$ pace is followed by a 300 m interval at 80% pace, a 200 m interval at 1500 meter pace is followed by a 200 m interval at 80% pace and a 100 m interval at top speed is followed by a 100 m interval at 80%. After a 400 m slowly paced recovery, the cycle can be repeated. This type of workout generally is aimed at improving the runner's speed at short distances but also helps improve the long-distance runner's bio-mechanics and efficiency.

FIG. 5c describes a typical hill workout. The runner would choose a hill of reasonable gradient and appropriate length and then repeat the "long" 600 m hill twice at a pace similar to the track equivalent of 5 Kilometer pace, the runner jogging easily down the hill to recover, followed by four to eight repeats of a shorter 200 m hill, the recovery again consisting of jogging back to the base of the hill. Hill workouts improve aerobic conditioning rapidly and also present a very low risk of injury to the participating runner. As bodily impact is reduced during the climbing portion of the interval (each foot has a shorter distance to "drop" as the runner ascends than the runner would experience on flat ground), chances of injury, despite high intensity, are reduced, especially when compared to an interval workout of equivalent length and duration.

FIG. 5d illustrates another possible workout, a Lane 8 tempo run. All running tracks stagger the start of the runners in the different lanes to account for the longer distance that runners in the outer lanes actually run. In this workout, this stagger start is exploited. The runner runs in lane 8, starting at the marked stagger start and runs 400 m at 10K pace, finishing at the track's normal and marked finishing line. The distance from the finishing line back to the lane 8 stagger start provides a brief recovery to the runner. The short recoveries involved in this workout and the relatively fast pace of the intervals increase aerobic condition and running efficiency.

Figure 5:
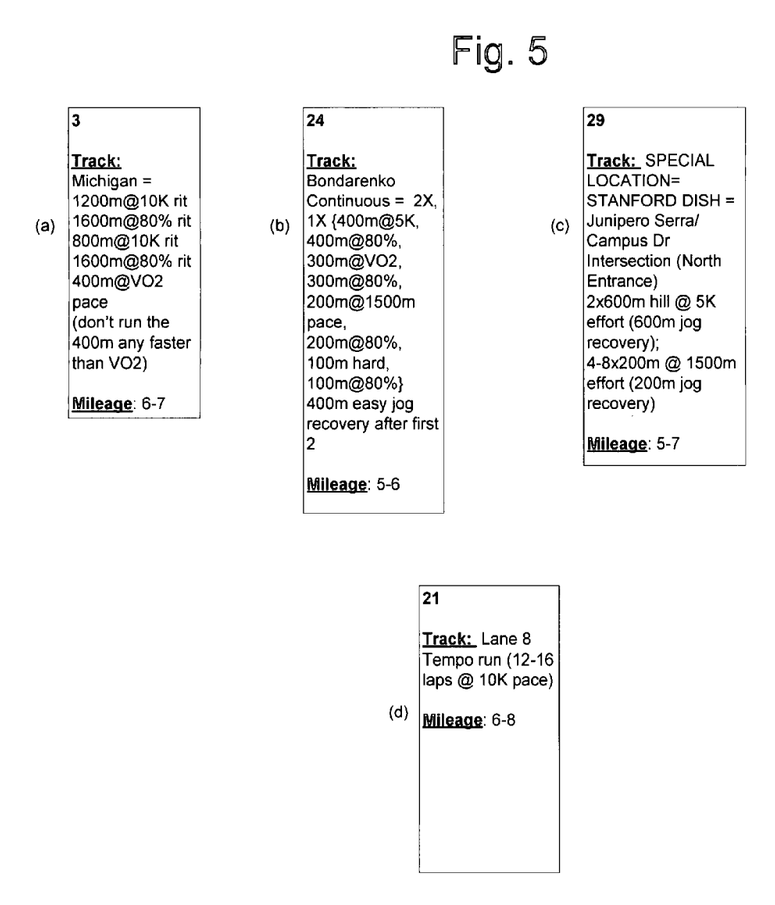
FIGS. 5a, 5b, 5c and 5d illustrates exemplary workouts contained in the workout database illustrated in FIG. 2 in accordance with an embodiment of the present invention.
Figure 7:
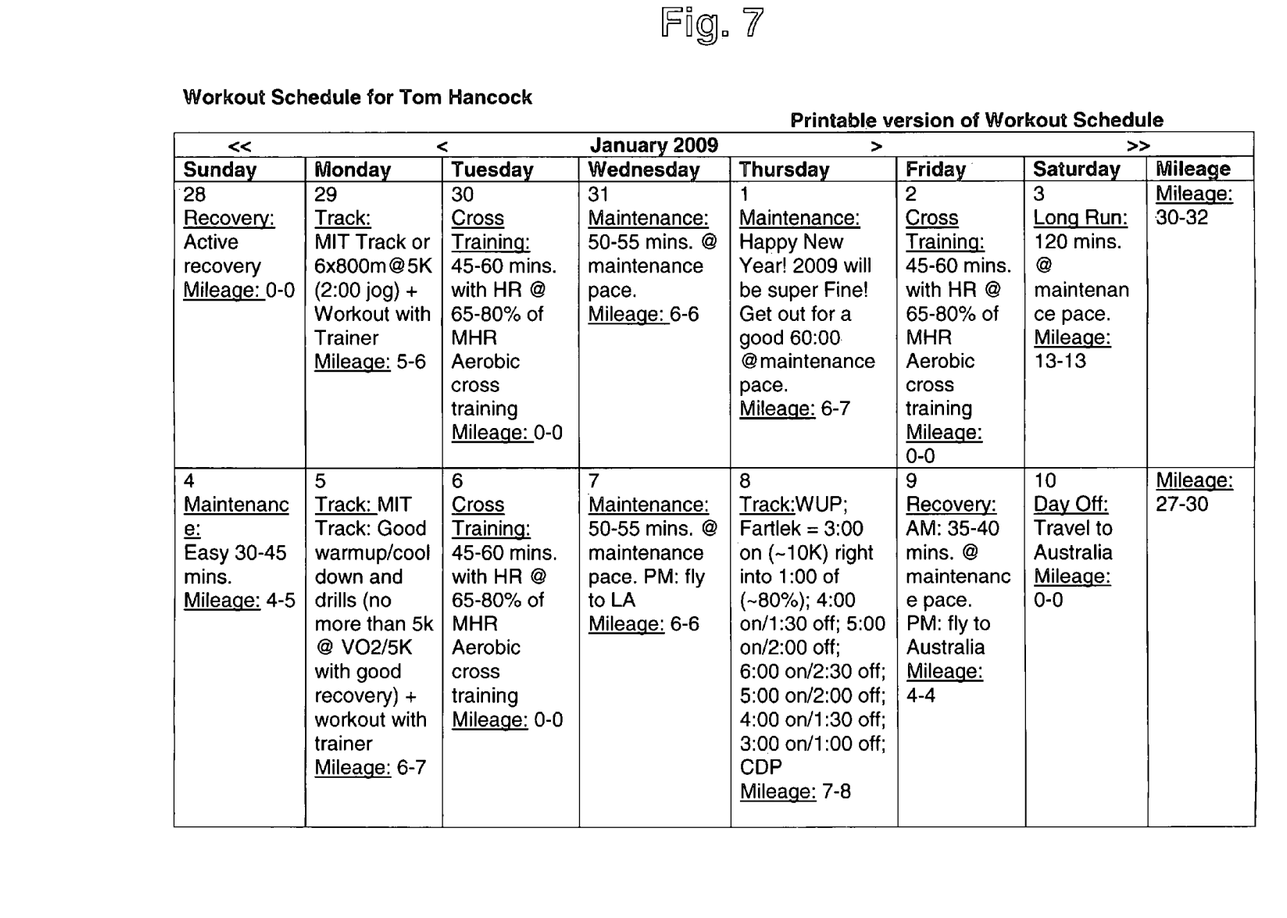
FIG. 7 is a sample workout schedule prepared for a runner using an embodiment of the present invention.

The workouts illustrated in FIG. 5 are representative and not comprehensive. Each may be themselves varied. They were chosen for detailed discussion as merely stating them in a chart would not necessarily make the workout obvious. Other simpler workouts, shown in the sample workout schedule shown in FIG. 7 require less explication. For example, a 6 mile run at maintenance pace is self-explanatory.

Having now calculated the total week mileage and allocated that mileage among the different types of workouts necessary to prepare the runner for his or her chosen race, schedule generation engine 120 selects appropriate workouts of each type from the workout database 140 at step 131 (FIG. 3b).

Figure 6:
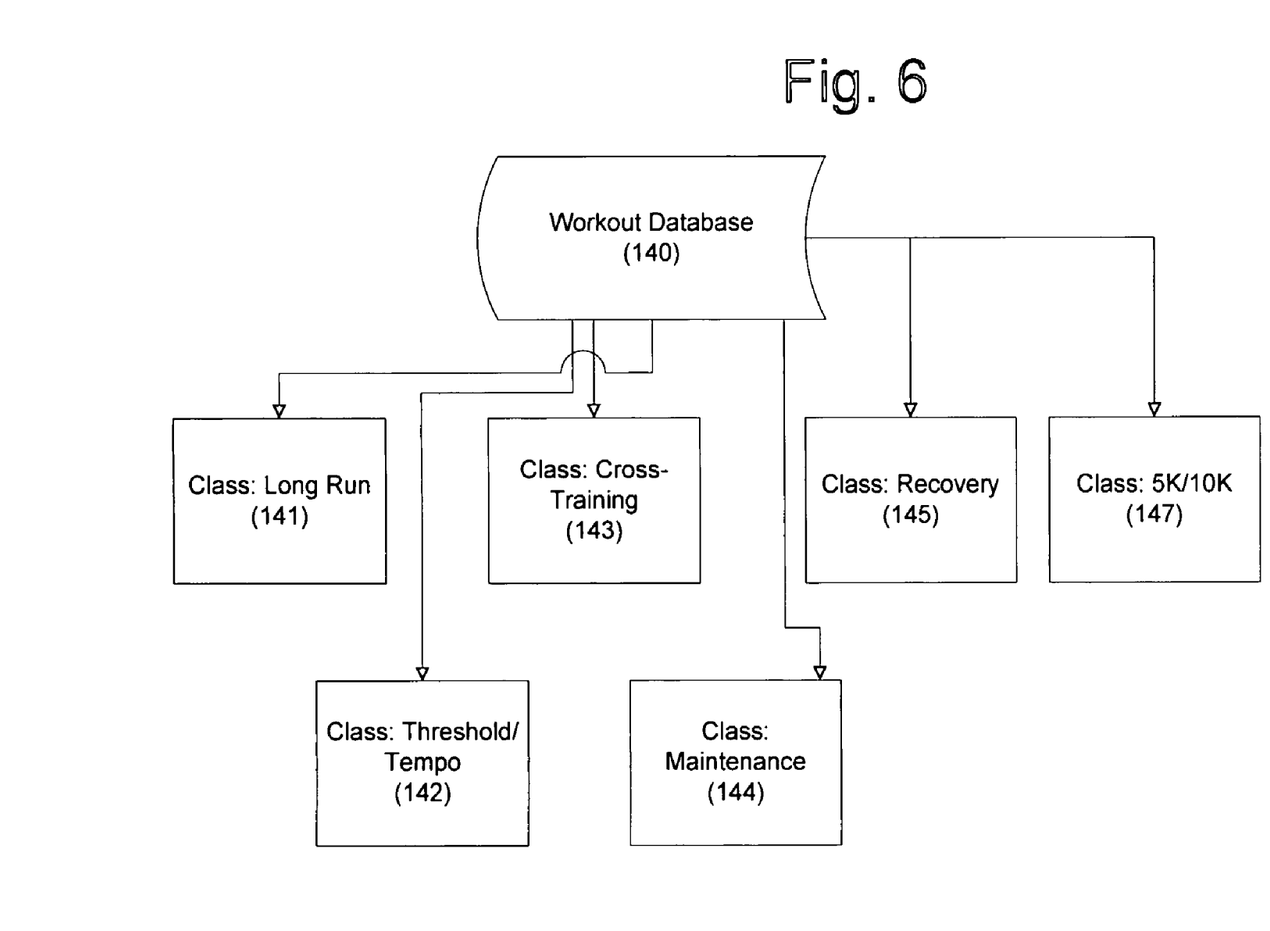
FIG. 6 is a detail of the workout database shown in FIG. 2, further illustrating the structure of the database according to an embodiment of the present invention.

FIG. 6 details how workout database 140 is structured. Each item in the database (at present, in the first embodiment of the present invention, database 140 contains approximately 60,000 different workouts) is sorted by class. In FIG. 6 the workout database 140 has been sectioned into a long run class 141, a threshold/tempo class 142, a cross-training class 143, a maintenance class 144, a recovery class 145 and a 5K/10K class 147. Schedule generation engine 120 will pull required workouts from database 140 according to the needed class of workouts. Each class of database 140 has many different workouts of that class. For example, in long run class 141, the workouts might range from an intro workout of perhaps 8 miles at maintenance pace to a serious Marathon preparation run of 22 miles, the first 18 at maintenance pace and the last 4 at Marathon goal pace. Nothing herein should be taken to limit database 140 to only these six classes. Fewer or more classes might be useful in particular circumstances and can be readily accommodated by the present invention.

Once schedule generation engine 120 has populated a schedule with particular workouts from database 140 and formatted the data appropriately, a monthly schedule is presented to the runner by means of the user schedule and use engine 160. The runner can review the schedule, send messages to the coach (if available) for clarification or modification, etc. In an embodiment of the present invention, the system permits the runner to contact other runners to run with and flags those workouts the runner shares with other local users of the present invention. This provides for seamless collaboration and peer to peer support as members share common terms and similar schedules.

The foregoing descriptions of embodiments of the present invention have been presented for purposes of illustration and description only. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A non-transitory computer-program product for use in conjunction with a computer system, the computer-program product comprising a computer-readable storage medium and a computer-program mechanism embedded therein for automatically generating an athletic training schedule, the computer-program mechanism comprising:
    a pace chart generator for accepting user data including at least a first time for a measured course and generating a series of paces for the user to run, the paces being based on the user's current physical conditioning level as demonstrated by the at least first time over a measured distance;
    a schedule generator for accepting the paces generated by the pace chart generator and at least a first projected race, assigning concomitant athlete level, and populating a training calendar based on the series of paces generated by the pace chart generator, the concomitant athlete level and the at least first projected race; and
    a pre-populated sealed workout database for providing workouts of different classes to the schedule generator for populating the training calendar, the workouts in the workout database each being minimally classified as to intensity, physiological target, mileage range, associated pace and training phase period, the workouts being chosen by the schedule generator based on both the amount of time available before the at least first projected race and the type of race that the first projected race is; and wherein the schedule generator re-populates the training calendar automatically by selecting workouts from the pre-populated sealed workout database at any time based on user input that indicates at least one of a race schedule addition, subtraction or change, missed training and an injury status change.

2. The computer-program product of claim 1 wherein the physiological target classification in the workout database classes includes $VO_2$ maximum, lactate threshold, aerobic threshold, biomechanical efficiency and oxygen economy.

3. The computer-program product of claim 2 wherein user input of injury status, subtraction, addition of a new race, change to the first projected race and missed workouts causes the schedule generator to populate the training calendar with different workouts from the pre-populated workout database to compensate for the user's injury status and missed training.

4. The computer-program product of claim 1 wherein a third party is permitted access to review each training calendar populated by the schedule generator 5. The computer-program product of claim 4 wherein the user can permit any number of third parties to access and view the user's training calendar to coordinate training together.

6. The computer-program product of claim 1 wherein the pace chart generator automatically recalculates the series of paces each time the user enters additional time for measured distance information and automatically updates the training schedule with new workouts if the new time indicates a new fitness level.

7. A system for automatically creating a personalized training plan comprising:
    a user preference input module wherein the module accepts user data including at least a time trial result and a training goal, the goal further including at least a first race at a first distance;
    a pace tracking module which accepts the user time trial result and generates at least a first pace chart;
    a sealed pre-populated workout database containing a plurality of workouts classified at least as to the type of race that each workout is optimized to prepare a racer for, intensity, physiological target, mileage range, associated pace and training phase period; and
    a personalized training plan generation module coupled to both the pace tracking module and the pre-loaded sealed workout database which accepts the user data and the pace chart and populates a training calendar with workouts from the database appropriate to meet the training goal, if sufficient time exists between when the user data is received and the date of the at least first race.

8. The system of claim 7 wherein the physiological targets associated with the workouts in the pre-populated workout profile database include at least $VO_2$ maximum, lactate threshold, aerobic threshold, biomechanical efficiency and oxygen economy.

9. The system of claim 8 wherein user input of at least one of injury status change, addition of an additional race, subtraction of a previously entered race, training log input which deviates below previously scheduled training causes the personalized training plan generation module to re-populate the training calendar differently according to the type and duration of the injury and other changes and further causes the system to indicate that training for the training goal is not appropriate if the type of injury or the duration of the injury preclude reaching the training goal safely.

10. The system of claim 7 wherein a third party is permitted to access and modify the training calendar.

11. The system of claim 10 wherein the user may permit any number of third parties to access and view the user's training schedule in order to coordinate training together.

12. The system of claim 7 wherein the pace chart is recalculated each time the user enters new time trial results.

13. A computer-implemented method for generating a personalized training plan, the method comprising the steps of:
  accepting as input from the at least first user an at least first future planned race distance, an at least first race date and an at least first time measured for running a course of known distance;
  generating pace metrics, using a pace chart generator, based on the time measured for running the course of known distance input;
  accepting as further input user training environment data;
  selecting from a pre-populated sealed workout database, using a schedule generator, workouts and distances that can prepare the first user to complete successfully the at least first race on the first race date, provided that the workouts are run at the pace metrics and the distances indicated by the workouts selected from the workout database and wherein the workouts in the pre-populated workout database are each minimally classified as to intensity, physiological target, mileage range, associated pace and training phase period; and
  generating as output a training plan comprising the workouts from the workout database and the pace metrics for the at least first user, the training plan being compiled by the schedule generator.

14. The method of claim 13 wherein the physiological targets of the workouts in the pre-populated workout database include at least $VO_2$ maximum, lactate threshold, aerobic threshold, biomechanical efficiency and oxygen economy.

15. The method of claim 14 wherein the user may additionally input injury nature and status information and wherein the training plan will be altered to accommodate the injury nature and duration.

16. The method of claim 13 wherein a third party is permitted to access the training plan and modify it prior to the training plan being presented to the user.

17. The method of claim 16 wherein the user may grant access to the user's training plan to any number of third parties in order to coordinate training together.

18. The method of claim 13 wherein the step of generating pace metrics is repeated each time new race distance and time information is accepted.

* * * * *